United States Patent
Boenisch

(10) Patent No.: US 8,536,860 B2
(45) Date of Patent: Sep. 17, 2013

(54) METHOD AND APPARATUS FOR NON-DESTRUCTIVE TESTING

(75) Inventor: Andreas Boenisch, Schwamstedt (DE)

(73) Assignee: Innospection Group Limited (GB)

( * ) Notice: Subject to any disclaimer, the term of this patent is extended or adjusted under 35 U.S.C. 154(b) by 687 days.

(21) Appl. No.: 12/524,700

(22) PCT Filed: Jan. 28, 2008

(86) PCT No.: PCT/GB2008/000288
§ 371 (c)(1),
(2), (4) Date: Jul. 27, 2009

(87) PCT Pub. No.: WO2008/090370
PCT Pub. Date: Jul. 31, 2008

(65) Prior Publication Data
US 2010/0102808 A1   Apr. 29, 2010

(30) Foreign Application Priority Data
Jan. 27, 2007 (DE) .................. 10 2007 004 223

(51) Int. Cl.
*G01N 27/90* (2006.01)
*G01R 33/12* (2006.01)

(52) U.S. Cl.
USPC ............ 324/221; 324/232; 324/220; 324/242

(58) Field of Classification Search
USPC .......................... 324/240, 220, 221, 232, 242
See application file for complete search history.

(56) References Cited

U.S. PATENT DOCUMENTS

| | | | |
|---|---|---|---|
| 2,194,537 A | 3/1940 | Adams | |
| 2,573,799 A | 11/1951 | MacLean | |
| 3,060,377 A | 10/1962 | Schmidt | |
| 3,693,075 A * | 9/1972 | Forster | 324/229 |
| 3,916,302 A * | 10/1975 | Madewell | 324/220 |
| 4,621,532 A * | 11/1986 | Takagi et al. | 73/623 |

(Continued)

FOREIGN PATENT DOCUMENTS

| | | |
|---|---|---|
| DE | 2645274 A1 | 4/1977 |
| DE | 29608664 U1 | 9/1997 |

(Continued)

OTHER PUBLICATIONS

International Search Report for International Application No. PCT/GB2008/000288 dated Jul. 10, 2008 (3 pages).
International Preliminary Report on Patentability for International Application No. PCT/GB2008/000288 dated Apr. 7, 2009 (6 pages).

(Continued)

*Primary Examiner* — Jay Patidar
(74) *Attorney, Agent, or Firm* — Schmeiser, Olsen & Watts, LLP

(57) ABSTRACT

A method and apparatus in which at least two different test phases are performed on a test object, selected from: conventional eddy current testing, partial saturation eddy current testing, and ultrasonic testing. Measurement data sets are obtained from the at least two different test phases, with each measurement data set comprising measurement data corresponding to a plurality of test positions. The data sets are combined in a data processing means and the combined measurement data is processed to evaluate a damage condition of the test object. In a preferred embodiment, all of conventional eddy current testing, partial saturation eddy current testing, and ultrasonic testing are performed. The apparatus may be provided in two or more sub-assemblies, of which one may be an internal test tool and one may be an external tool. Alternatively, the apparatus may be capable of carrying out all three of the test phases.

35 Claims, 5 Drawing Sheets

(56) References Cited

U.S. PATENT DOCUMENTS

| | | | |
|---|---|---|---|
| 4,878,180 A * | 10/1989 | McWhirter et al. | 702/34 |
| 4,955,235 A * | 9/1990 | Metala et al. | 73/601 |
| 5,117,182 A * | 5/1992 | Cecco et al. | 324/220 |
| 5,285,689 A | 2/1994 | Hapstack et al. | |
| 5,345,514 A * | 9/1994 | Mahdavieh et al. | 382/152 |
| 5,479,100 A * | 12/1995 | Fowler et al. | 324/263 |
| 5,628,667 A | 5/1997 | Levi | |
| 5,751,144 A * | 5/1998 | Weischedel | 324/240 |
| 5,850,034 A * | 12/1998 | Hugens, Jr. | 73/19.07 |
| 6,344,739 B1 * | 2/2002 | Hardy et al. | 324/220 |
| 7,518,359 B2 * | 4/2009 | Wang et al. | 324/238 |

FOREIGN PATENT DOCUMENTS

| | | |
|---|---|---|
| DE | 10237980 A1 | 7/2003 |
| EP | 0301906 A | 2/1989 |
| EP | 1063521 A1 | 12/2000 |
| EP | 1717412 A1 | 2/2006 |
| WO | 2007130662 A2 | 11/2007 |

OTHER PUBLICATIONS

Sadek H.M. "NDE Technologies for the Examination of Heat Exchangers and Boiler Tubes-Principles, Advantages and Limitations", INSIGHT vol. 48, No. 3, Mar. 1, 2006, pp. 181-183, XP002486275.

* cited by examiner

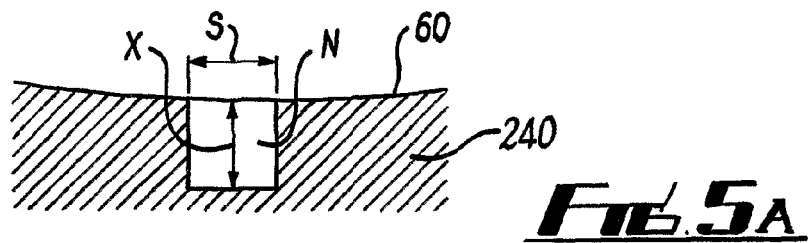
FIG. 5A
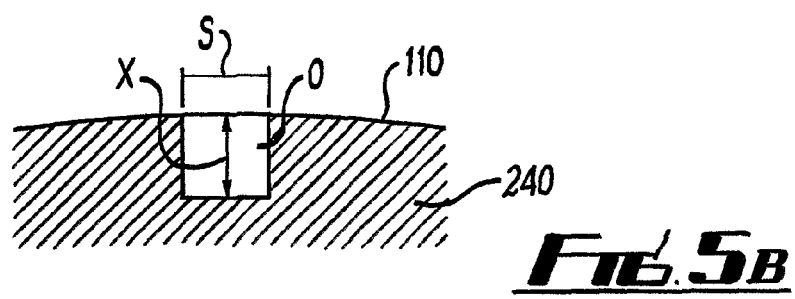
FIG. 5B
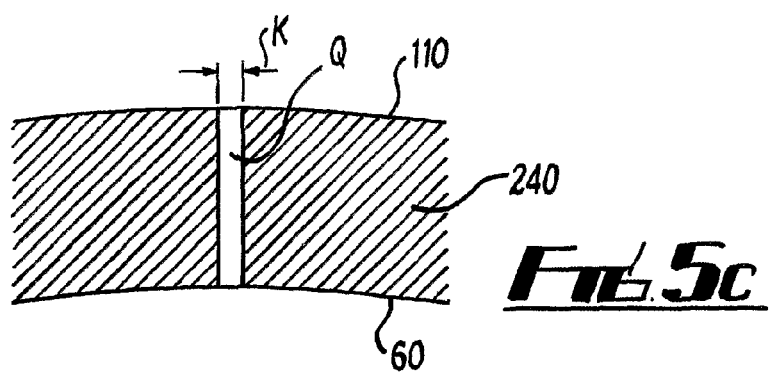
FIG. 5C
| | T % | R mm | W mm | Z mm |
|---|---|---|---|---|
| L2 | 5 | 50 | 1 | 1.5 |
| L3 | 10 | 50 | 1 | 3.2 |
| L4 | 12.5 | 50 | 1 | 3.2 |
FIG. 6

METHOD AND APPARATUS FOR NON-DESTRUCTIVE TESTING

The invention relates to a method and an apparatus for the non-destructive testing of prefabricated parts, such as those used for the exploration and equipping of oil and gas fields and for the construction of pipelines and geothermal bores.

Methods and apparatus for the non-destructive testing of tubulars or similar materials are known, and in particular are carried out using ultrasonic measuring techniques or the eddy current measuring techniques. Provision is made for these testing methods as part of quality control processes which are applied during production and use of metallic conductive products such as tubulars, rods, profiles, wire and the like. For this purpose, the user employs testing apparatus having particular sensor arrangements having either ultrasonic sensors or eddy current sensors, so that the quality control process, which is performed by manual comparison to reference data, produces a test report which the manufacturer can make available when prefabricated parts are supplied.

However, it has been found that particular sets of measurement data which are obtained with testing apparatus of this kind based on a particular sensor arrangement fail to pick up residual faults in the form of minor material damage, slight changes in the material and/or slight reductions of wall thickness. For this reason, companies which make use of prefabricated tubulars which are intended for long-term applications, particularly in the area of oil fields are demanding additional tests which have, to date, been labour intensive and time-consuming.

The invention is concerned with the problem of providing a method and an apparatus suitable for the non-destructive testing of tubular components in the form of prefabricated parts for oil fields, in which more accurate information on damage can be obtained with little technical effort or complication. The invention is also concerned with the problem of providing a method and apparatus for the non-destructive testing of tubular components with greater productivity. The invention is also concerned with the problem of providing a technique in which it is possible to use an apparatus for metal prefabricated parts of substantially any desired type, and which can easily be handled on site. The invention is also concerned with the problem of providing a method and apparatus in which the said prefabricated parts can be selected with great reliability.

More generally it is an aim and object of the invention to provide a method and apparatus which overcomes or mitigates the drawbacks of prior art non-destructive testing techniques.

According to first aspect of the invention, there is provided a method for the non-destructive testing of tubular components made of electrically conductive material, the method comprising the steps of:

Performing at least two different test phases on a test object, the test phases selected from the group comprising: conventional eddy current testing, partial saturation eddy current testing, and ultrasonic testing;

Obtaining a measurement data set from the at least two different test phases, each measurement data set comprising measurement data corresponding to a plurality of test positions;

Combining the measurement data sets in a data processing means and processing the combined measurement data to evaluate a damage condition of the test object.

The method may comprise the step of performing conventional eddy current testing and partial saturation eddy current testing on the test object. Preferably, the method comprises the step of performing at least three test phases, the test phases selected from the group comprising: conventional eddy current testing, partial saturation eddy current testing, and ultrasonic testing. More preferably, the method comprises performing conventional eddy current testing, a partial saturation eddy current testing, and ultrasonics testing. In other words, all three test phases are performed.

The method may comprise the additional step of selecting or rejecting the test object for further use according to the evaluated damage condition. Alternatively, the method may comprise the step classifying the test object according to the evaluated damage condition. A tubular may for example be classified for a lower grade of use or approved for a particular application.

The method may comprise a global comparison of measurement data from the test object by the data-processing means when evaluating the damage condition. The data processing means may evaluate the overall condition of the test object by analysing the results of the multiple test phases.

The prefabricated parts may be rejected if a limit value is exceeded in one of the at least two test phases.

The total number of defects identified in the combined measurement data may be used when evaluating the damage condition. In this way, the method may, for example, reject a test object because the frequency of identified defects exceeds a threshold. Alternatively or in addition, the spatial distribution of defects identified in the combined measurement data may be used when evaluating a damage condition.

According to one embodiment, a comparison of measurement data from the at least two test phases at a test position is performed by the data-processing means on the test object when evaluating the damage condition. Thus the method involves verifying a potential damage condition at a particular location by correlating the data with data obtained from another of the test phases. This offers the advantage that an event which is not clearly indicated as a defect by one test phase, for example due to the test phase being weak at indicating a category of defect, can be cross-referenced to measurement data from the other test phases. This allows more accurate determination of marginal damage conditions, without relying on the interpretation of an operator of the test equipment.

The method may take measurements at plurality of test positions are pre-assigned to the data processing means.

In one embodiment, at least two test phases are performed simultaneously. Alternatively or in addition, two test phases may be performed consecutively.

The test objects may be evaluated against quality criteria assigned to the data processing means. The test objects may be evaluated against quality criteria which are configurable in the data processing means as analysis thresholds.

The test object may be a tubular and at least one of the test phases may be performed from the interior of the tubular. Alternatively or in addition, at least one of the test phases may be performed from the exterior of the tubular.

The test phases to be performed may be selected in dependence on the diameter and/or wall thickness of the test object. Whether the test phases are performed from the interior or the exterior of the test object may be dependent on the diameter and/or wall thickness of the test object.

In one embodiment, the conventional eddy current test and an ultrasonic test take place from the interior of the tubular and the partial saturation eddy current test may be performed from the outer circumference of the tubular.

The method may comprise the step of performing an additional ultrasonic test from the exterior of the test object.

The first test phase may be performed from the interior of the tubular and may cover the entire cross-section of the tubular in a single pass of the tubular. A test phase may take place on the outer circumference of the tubular, and may consist of a single pass of the tubular.

A test phase may take place on the outer circumference of the tubular, and may comprise plurality of circumferentially offset passes of the tubular.

Preferably, a conventional eddy current testing phase is carried out in a frequency range of 10 kHz to 350 kHz, more preferably, 50 kHz to 300 kHz, most preferably 100 kHz to 300 kHz.

Preferably, a partial saturation eddy current testing phase is carried out in a frequency range of 10 kHz to 150 kHz, more preferably, 10 kHz to 100 kHz, most preferably 50 kHz to 100 kHz.

According to a second aspect of the invention, there is provided apparatus for the non-destructive testing of tubular components, the apparatus comprising sensing apparatus configured to perform at least two different tests on a test object, the tests selected from: a conventional eddy current test, a partial saturation eddy current test, and an ultrasonics test; and a data-processing means configured to process combined data from at least two measurement data sets from the different tests to evaluate a damage condition of the test object.

The apparatus may comprise a plurality of test components, and each component may be configured to perform one of a conventional eddy current test, a partial saturation eddy current test, and an ultrasonics test. The test components may be connected to the data-processing means via a multi-channel multiplexer.

The test components may be operated on a plurality of sub-assemblies. Alternatively, the test components may be operated on a single assembly.

The apparatus may comprise a sub-assembly configured for interior operation in a test object and may further comprise a sub-assembly configured for exterior operation on a test object.

The data processing means may be provided with respective programmable plug-in cards which receive the measurement data. The apparatus may also comprise means for outputting test report parameters, storing the measurement data which classifies the test object as a document, storing the data in the form of a complex test report and/or outputting the data as a warning signal, or as a display representation.

The apparatus may comprise means for registering measurement data according to test position, which may be an encoder.

According to a third aspect of the invention, there is provided a method of evaluating a damage condition of a test object, the method comprising the steps of:

Combining the measurement data sets obtained from at least two different test phases on a test object, the test phases selected from the group comprising: conventional eddy current testing, partial saturation eddy current testing, and ultrasonic testing, and each measurement data set comprising measurement data corresponding to a plurality of test positions, and;

Processing the combined measurement data to evaluate a damage condition of the test object.

According to a fourth aspect of the invention, there is provided a computer program product bearing machine readable instructions for implementing the method of evaluating a damage condition of a test object according to the third aspect.

According to a fifth aspect of the invention, there is provided a computer apparatus loaded with machine readable instructions for implementing the method of evaluating a damage condition of a test object according to the third aspect.

Embodiments of the second, third, fourth or fifth aspects of the invention may comprise essential, preferred or optional features of the first aspect of the invention as herein defined.

Although in aspects of the invention, the methods and apparatus include the performance of two test phases, preferred embodiments include the performance of at least three test phases. Thus according to a sixth aspect of the invention there is provided a method for the non-destructive testing of casing tubes, riser tubes, pipes, drilling strings or similar prefabricated parts made of electrically conductive material for exploration, equipping and transporting operations on oil and gas fields and for producing pipelines and geothermal bores, whereby said prefabricated parts being inspected and evaluated as individual test objects prior to installation and rejected if damage is found which exceeds a limit value, characterised in that at least three test phases are performed on the given test object by means of conventional eddy current testing, saturation eddy current testing and ultrasonic testing, and when so doing registers respective test positions with damage information along pre-assigned test distances, combines these as the respective measured data from the three tests in a data processing means, and subsequently processes all measured data using a computer program.

The method may comprise an object-related overall comparison is performed by the data-processing means and, in accordance with this triple evaluation of damage at the respective test positions, the test objects are selected as prefabricated parts for further use.

The method may be characterised in that the prefabricated parts are rejected as soon as a limit value is exceeded in one of the three test phases.

The three test phases may be performed simultaneously at a test position. Alternatively the three test phases are performed in succession at a test position.

The test objects are evaluated against respective quality criteria assignable to the program. The test objects may be evaluated against respective quality criteria which can be entered in the computer program as analysis thresholds.

Where a test covers the wall of the tubular prefabricated parts, the three test phases are optionally performed from the interior of the tubular and/or from the outside of the tubular. The test phases may be performed in dependence on the diameter or wall thickness of the prefabricated part.

In one embodiment, the eddy current test and an ultrasonic test take place from the interior of the tubular and the saturation eddy current test is performed from the outer circumference of the tubular. In another embodiment, an additional ultrasonic test is performed from the outer circumference of the test object.

A test from the interior of the tube may be performed as the first test phase and may cover the entire cross-section of the tubular. Preferably, in a test phase which takes place on the outer circumference of the tube only one test step is performed or a plurality of radially offset test steps are performed, depending on the diameter of the prefabricated part.

According to the seventh aspect of the invention there is provided an apparatus for the non-destructive testing of tubulars or similar prefabricated parts according to the first aspect, characterised in that a testing unit of the apparatus comprises at least three sensor sub-assemblies which perform a conventional eddy current test, a saturation eddy current test and an ultrasonic test, and a data-processing means which combines positionally accurately registered data from the three sensor sub-assemblies to give an expanded statement of damage.

The measurement data from the sensor sub-assemblies may be logged in a stepping sensor controller and/or of an eight-channel testing unit and can be transmitted to the data-processing means in order to classify the test object.

The sensor sub-assemblies may be connected to the data-processing means via a multi-channel multiplexer. The data processing means may be provided with respective programmable plug-in cards which receive the measurement data.

In one embodiment, the measurement data which classifies the test object is stored as a document in the form of a complex test report and/or output as a warning signal, as a display representation, or as similar output parameters.

In the method according to the invention, an eddy current test, a saturation eddy current test and an ultrasonics test may be matched to one another in such a way that it is possible make a more accurate assessment of the quality of the prefabricated part, or the amount of damage it has by combining respective sets of measurement data from these at least three tests.

The sets of measurement data which are produced in the tests may be associated in a positionally accurate manner with respective instances of damage on the test object, thus making possible a complex evaluation of the data in an evaluating unit with little cost and complication in the measurement. This increases the accuracy achieved in assessing faults in components so that there is an overall improvement in the quality control on prefabricated parts immediately before their use or application in the oil field, and thus enables consequential damage to be avoided.

The method according to the invention can be used with high productivity and reliability immediately before oil fields are equipped. In this case, the test objects are inspected immediately before they are used and any likely faults are detected. By means of software integrated with the testing unit, more specifically in the data-processing means, the test objects are evaluated against pre-assigned quality criteria and are made available after being classified in an optimal manner. For this purpose, special analysis thresholds are pre-assigned to the computer program as evaluation criteria, and on the basis of these evaluation criteria, the damage parameters which are detected can also be visually displayed. By the presetting of respective "rejection thresholds" (or analysis thresholds), quality criteria are implemented by means of software, while the range or respective sizes of the criteria, for example a maximum measurement of a given depth of damage, can be flexibly preset on a user-specific basis.

A complex damage analysis using the computer program of the testing unit is possible by virtue of the fact that the sets of measurement data which are obtained by means of the testing techniques or test phases are integrated at the site for the evaluation. In one embodiment, by making a direct comparison, it can be quickly established whether the analysis thresholds selected have been exceeded.

In one embodiment, the program is used to produce a direct indication on the display of the data-processing system of an object tested is detected to be faulty. This may be for example by a displaying a contrasting colour, or by generating a warning signal. More particularly, provision may be made for the test result obtained to be output in the form of a coloured representation of the whole of the tubular tested, from which it becomes possible for the object tested to be objectively evaluated. Provision may also be made for the exceeding of a threshold to be used as an output signal which triggers the software to generate a visible or audible signal directly on the testing computer or the display of the testing unit.

The given test specifications or analysis thresholds relate for example to the maximum reductions in wall thickness, craters, cavities, cracks or similar flaws which can be tolerated, which are evaluated in comparison with the nominal wall thickness of the tube being tested. These different evaluation thresholds or analysis thresholds may be preset in the program, thus enabling tubulars to be sorted by different quality requirements and enabling further use to be made of them in a user-specific way in accordance with risk categories or similar installation criteria.

The apparatus provided for performing the method takes the form of, in particular, a mobile testing unit with which the three testing processes can be used in combination in such a way that positionally accurate non-destructive testing is possible even in a single operation and the time taken by the quality control process is thus reduced. This complex material testing of tubulars, drilling stings and similar prefabricated parts is directed at improved detection of material damage, material changes and fluctuations in wall thickness in and on the prefabricated parts which are made available. The data sets from the respective steps of testing, which may be from the single testing pass, are logged in a data-processing means which co-operates with the apparatus. Documentation of the damage can then be supplied which in comparison with the known individual measurements is expanded and more precise. In particular, testing of tubulars or similar prefabricated parts made from different materials, and even from alloy steel for example, is made possible.

When the eddy current testing technique is used as a first test phase, eddy current sensors in a bridge circuit are guided over the prefabricated part in the longitudinal and circumferential directions in such a way that both changes in the layer of material or the material of the tubular wall and damage to the material are detected in the relevant position relative to the longitudinal axis of the object tested. What happens in this case is that the eddy current sensors, which are connected to an eddy current generator whose frequency can be varied, generate an induced secondary field in the wall of the tubular or in the surface of the tubular. Variations to or damage in the material at the surface produce corresponding changes in the secondary field in the region concerned and the impedance of the eddy current sensor to be influenced by the secondary field. This change in impedance is sensed in an indicator unit, for example an oscilloscope, and after processing in the testing unit, a positionally accurate assessment of condition can be derived from the given amplitude or phase of the signal and from the changes in it, which can be logged digitally.

In a second (i.e. parallel) step of testing, the principle of partial saturation eddy current testing is applied. Eddy current sensors in a bridge circuit are positioned between the poles of a DC magnet in the longitudinal direction of the axis of the prefabricated part, i.e. of the axis of the tubular. The DC magnet, which is adapted to be parallel to the surface of the material, generates particular magnetic field lines between the poles of the magnet, with a corresponding flux density being obtained along the magnetic field lines. In addition to these magnetic field lines, the eddy current sensors also induce a secondary field. Changes in or instances of damage to the material change the flux density of the magnetic field lines generated by the DC magnets, and the magnetic field lines in turn cause a change in the secondary field generated by the eddy current sensors. In turn a change is produced in the impedance of the eddy current source and by sensing the amplitudes or phases of the signals concerned, corresponding changes in the test piece, which can be sensed in a positionally accurate way, can be inferred and can be evaluated in the testing unit.

In this embodiment it is envisaged that an assessment of condition can be made relative to a calibration of reference samples, on an oscilloscope comprised in the eddy current testing unit. The measurement data from signal amplitude and signal phase which is generated by this partial saturation eddy current technique is fed into the data-processing means and is used to determine the changes in or instances of damage to the material with their positions accurately located.

A third (parallel) test phase is an ultrasonic technique employing roller-equipped testing heads, whereby a conventional analysis of an acoustic pulse is performed by means of the echo pulse which follows it. By means of an oscilloscope, this reflection is shown as an amplitude, and a measurement of thickness is derivable from the measured values. Ultrasonic testing heads are advantageously used for perpendicular sounding having a 5 MHz sensor/receiver system. In this embodiment, the ultrasonic testing head is provided in a rolling wheel, with an elastic body of rubber or a liquid serving as a coupling agent with the surface of the wall. It is thus possible for dry coupling to be used for the roller-equipped test heads and for the thickness of the tubular wall to be determined. The arrangement of a plurality of roller-equipped testing heads extending in parallel in the circumferential direction of the test object results in a correspondingly broad scanning field so that the entire circumference of the prefabricated part can be registered in a few test cycles. The corresponding data can be combined in the testing unit with the sets of information from the first and second test phases, resulting in a complex picture of the damage for assessment purposes.

Further details and advantageous embodiments of the invention can be seen from the following description and the drawings, of which:

FIGS. 5A to 5C are sectional representations of artificial reference marks according to a calibration standard, and;

FIG. 6 is an evaluation table for API specification for the testing of tubulars;

Figure 1:
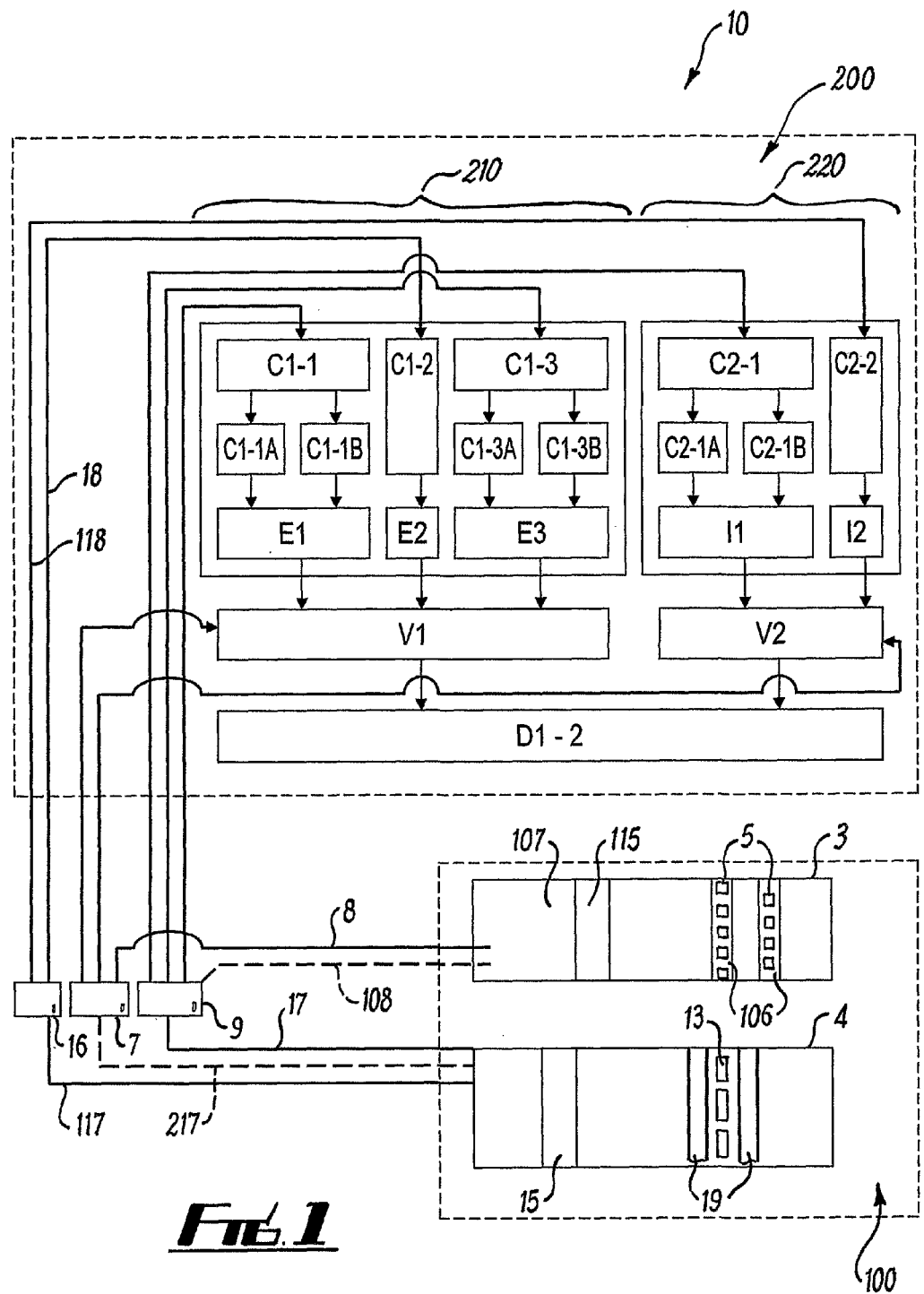
FIG. 1 is schematic view of a system including a testing apparatus and a data-processing means in accordance with a first embodiment of the invention.
Figure 3:
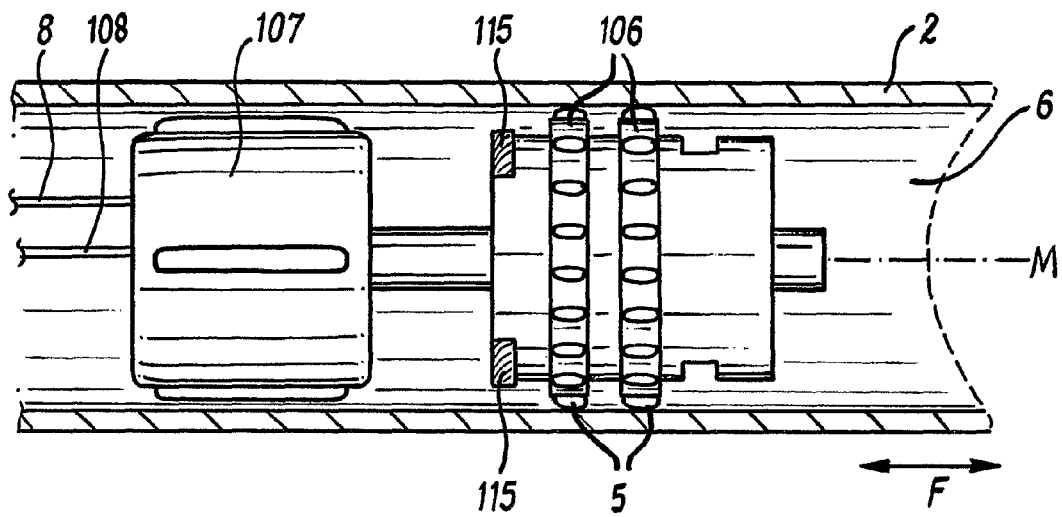
FIG. 3 is a schematic view of a part of the apparatus of FIG. 1 for making measurements in the interior of a tubular.
Figure 4:
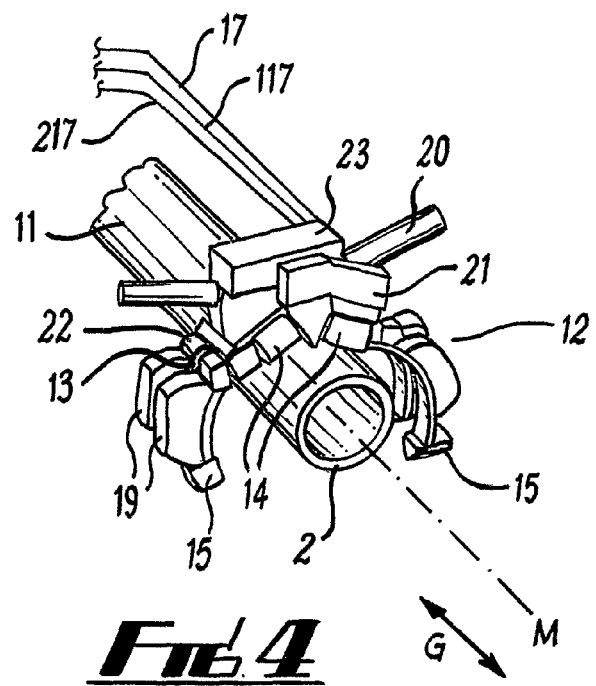
FIG. 4 is detailed view of a part of the apparatus of FIG. 1 for making measurements on the exterior of a tubular.

Referring firstly to FIG. 1 of the drawings, there is shown generally depicted at 10, a system in accordance with a first embodiment of the invention, comprising a test apparatus 100 and a data processing means 200. The testing apparatus 100 is provided with appropriate sensors for eddy current testing, partial saturation eddy current testing and ultrasonic testing. In this example, the test apparatus is described with reference to applications in the testing of tubulars, which are prefabricated parts intended for use in an oil or gas field. The test apparatus 100 comprises two sub-assemblies; an internal sub-assembly 3 which can be displaced inside the tubular, and a second, external sub-assembly 4. In this embodiment, the internal sub-assembly 3 is configured with eddy current sensors 5, and the second sub-assembly 4 is configured to perform a partial saturation eddy current measurement technique and an ultrasonic measurement technique. FIG. 1 shows sub-assemblies 3 and 4 schematically. FIGS. 3 and 4 respectively show sub-assemblies 3 and 4 in more detail.

As illustrated in FIGS. 1 and 3, individual eddy current sensors 5 are positioned on the sensor subassembly 3 next to one another around the circumference of a body. The eddy current sensors 5 are positioned in two rings 106 in such a way that complete coverage of the inside 6 of the tubular 2 is obtained by the two rings of sensors 106. A detection region which is radially closed is formed by the plurality of eddy current sensors 5. The sensors 5 have a width from 5 mm to 30 mm (preferably 20 mm) and are pressed against the inner circumference 6 of the tubular 2 in such a way that the requisite sensitivity is obtained.

In the embodiment shown in FIG. 3, the rings 106 of sensors are guided by means of rollers which are mounted at both ends on springs. The sensor sub-assembly 3 is connected in this case to a stepping motor 107 in the region of the sensor rings, by which the subassembly can be displaced in the direction defined by the longitudinal axis M of the tubular, as shown by arrow F. In a steel tubular, the movement F can be obtained by corresponding magnetisable wheels, shoes, runners or the like on the stepping motor 107. The stepping motor 107 is connected in turn to a stepping motor controller 7 by which the system is driven.

The testing sub-assembly 3 with eddy current sensors 5 can be connected by respective cables 8 and 108, as shown in FIG. 1, up to 50 m in length, to a multi-channel multiplexer 9 by which the respective impedance variations in the region of the eddy current sensor 5 are acquired and registered. Starting from this multiplexer 9, the corresponding sets of measurement data are transmitted, in timed succession, to a data-processing means 200. The data processing means 200 may advantageously take the form of a personal computer loaded with appropriate instructions or the like, and may be provided with a display, audio output section and other accessories.

The measurement data from the eddy current sensors 5 is conveniently carried out by means of PC cards which, by means of adapted software, allow the logged impedance states to be classified and, in particular, provide a representation of the individual channels of the multiplexer 9. The measurement signals thus processed in the form of changes in amplitude and phase at the individual sensors 5 permit, in particular, an analysis to be made of the state of the material in the wall of the prefabricated part 2.

A second testing sub-assembly 4 of the testing unit 100 is shown in FIGS. 1 and 4, and is configured to be operated on the outer surface 11 of a prefabricated part, and in particular a tubular 2. The testing sub-assembly 4 is equipped with non-contact roller-equipped testing-heads 12 for the performance of a partial saturation eddy current testing technique and an ultrasonic testing technique. In this case, eddy current sensors 13 are designed in a range of widths from 5 mm to 30 mm and are arranged substantially centrally between respective electromagnets or permanent magnets 19. Corresponding to the diameter of the tubular 2, the mountings of the magnets 19 and eddy current sensors 13 of the testing sub-assembly 4 may be so sized that the circumference of the prefabricated part can be covered over an arcuate range of from 90° to 360°.

The magnets 19 and the eddy current sensors 13 are held at a constant distance from the metal surface 11 by corresponding supporting rollers 14, with the eddy current sensors 13 being connected to the data processing means system by means of a connection 17 to the multi-channel multiplexer 9, as shown in FIG. 1. In this way, the signal amplitudes and phases from the individual sensors 13, 19 can be detected and used for evaluating the state of the material of the test object.

In addition, both the interior sub-assembly 3 the exterior sub-assembly 4 for testing the outside of the tubular 2 carry a variable number of roller-equipped ultrasonic testing heads 115, 15 respectively. The number of ultrasonic testing heads 115, 15 can be varied to suit the diameter of the prefabricated part 2. These non-contact roller-equipped testing heads 115, 15 are connected to an eight-channel ultrasonic unit 16 by a connection 117, as shown in FIGS. 1 and 4. The eight-channel ultrasonic testing unit 16 generates digital output signals which are transmitted to the data processing means 200 via connections 18, 118. In this way, the measured values from the ultrasonic testing heads 15 can be logged, digitised, and can be transmitted online (in real-time) to the data-processing means 200. The measurement data, relating for example to the wall thickness of the prefabricated part 2, can then be shown on the display (not shown) of the data processing means 200.

The magnetic heads 19 of the exterior sub-assembly 4 are held at a constant distance from the test object by the carrier parts 14 of the roller-equipped testing heads, which are mounted directly in front of the magnets 19. In the case of the interior sub-assembly 3, the respective rings having wheels offset around the circumference carry the annular eddy current sensors 5. Also provided is an additional ring which presses the roller-equipped testing heads against the inner surface 6 of the material of the tubular 2 at a constant applied pressure.

The exterior sub-assembly 4 is placed on the prefabricated part 2, the sensors 13 and magnets 19 in the region of the roller-equipped testing heads 12 are activated and the testing sub-assembly 4 can then be moved at constant speed in the direction defined by the longitudinal axis M of the tube, as shown by arrow G. A test of the tubular is therefore carried out during the movement of the testing sub-assembly 4 on the axis M of the tube, at which time an on-line (or real-time) evaluation of the recorded measurement data is also performed in the data-processing means 200. The testing sub-assembly 4 has in this example a longitudinal guide 20 which may be implemented for manual or motorised operation, and which co-operates with a corresponding position indicator 21 and/or a clamping system 22. A junction box 23 is provided with corresponding electrical connectors 17, 117, 217 to the data processing means 200 or the signal converters 7, 9, 16.

After the unit 4 is displaced over the length of the prefabricated part 2, the testing unit is moved in its circumferential direction and in a second testing pass, a further region of the prefabricated part 2 is traveled over. These steps are repeated until such time as the entire surface 11 of the tubular has been covered and registered. Thus, according to this embodiment of the invention, the internal test sub-assembly 3 performs a conventional eddy current test and an ultrasonic test, and the external test sub-assembly 4 performs a partial saturation eddy current test and an ultrasonic test.

All the data which are detected in the test phases and in the separate test passes can be passed directly to the data-processing means 200 or to its respective plug-in cards via the multiplexer 9 and the eight-channel ultrasound converter 16. This enables the system software of the data-processing means 200 or its plug-in cards to make an assessment of damage to the material, changes in material and/or changes in wall thickness in a short time period, as demonstrated by the flow charts of FIG. 1 or FIG. 2. The available data or data sets are stored in with appropriate identification and are made available to the customer, and also enable a subsequent analysis of the prefabricated part 2 to be made.

The processing of the measurement data which is logged in the data-processing means 200 according to one specific embodiment is illustrated in the flow chart of FIG. 1. The method can be adapted to suit the given prefabricated part 2 and is described in detail below only by way of example. In this example, the testing procedure is carried out using the apparatus as described with reference to FIGS. 3 and 4.

Referring to FIG. 1, the following sets of data are evaluated in a position comparison method, shown generally at 220, using the exterior testing sub-assembly 4. In step C1-1, the partial saturation eddy current measurement data is received in the data processing means 200, and the signal phases (step C1-1A) and the signal amplitude (step C1-1B) are evaluated individually. In this example, the analysing algorithm uses the signal phase (step C1-1A) to characterise a type of event anywhere in the wall of the tubular 2 and the signal amplitude (C1-1B) represents the order of magnitude of the event, the results indicated at evaluation E1.

In step C1-2, the thickness of the wall of the tube is derived from the ultrasonic transit time measurements acquired from sensors 15, indicated at evaluation E2.

In step C1-3, the signal phase (C1-3A) and the signal amplitude (C1-3B) of the measurement data from the conventional eddy current testing are evaluated individually.

Similar to step C1-1, the analysing algorithm uses the signal phase (step C1-3A) to characterise a type of event anywhere in the wall of the tubular 2 and the signal amplitude (C1-3B) represents the order of magnitude of the event, the results indicated at evaluation E3.

The evaluation of the data from C1-1, C1-2 and C1-3 is performed for the same position P with the object of making a comparison V1 of the common analyses of events and damage. The result is documented directly, and may be used in its own right to provide an assessment of material damage. However, in this embodiment it is used for comparison with an internal testing procedure, indicated generally at 220, carried out using sub-assembly 3.

In procedure 220, the sub-assembly 3 has eddy current sensors 5 in combination with ultrasonic sensors 115. Via the control unit 7, the motor-controlled drive module supplies the position P of the damage being evaluated to allow a positional combination with the data from the testing procedure 210. In procedure 220, the following sets of data are evaluated in a position comparison.

In step C2-1, the signal phase (C2-1A) and the signal amplitude (C2-1B) of the measurement data from the interior conventional eddy current testing are evaluated individually. Similar to step C1-1, the analysing algorithm uses the signal phase (step C2-1A) to characterise a type of event anywhere in the wall of the tubular 2 and the signal amplitude (step C2-1B) represents the order of magnitude of the event, the results indicated at evaluation I1.

In step C2-2 the thickness of the wall of the tube is derived from the ultrasonic transit time measurements acquired from sensors 115, indicated at evaluation I2. Step V2 is a comparison of the results of evaluations I1 and I2.

The system thus allows a common damage analysis to be made for procedure 210 (the external testing system) and procedure 220, (the internal testing system), and as result of this the positions P are compared with one another (steps V1 and V2), evaluated and documented (step D1-2) and/or indicated visually or audibly.

A high sensitivity of detection is achieved with the system of the invention and the individual evaluations of events or damage at steps C1-1, C1-2, C1-3, C2-1 and C2-2.

With the combination of features according to the invention, the following advantages over known testing systems may be achieved:
- an optimised damage pattern may be obtained;
- a distinction between different events, i.e. between damage of different types, is possible;

a higher sensitivity of testing for detecting very small damaged points is obtained, and;

a clearer classification of different flaws and thus an improved definition of the boundary between the rejection and acceptance of a tubular is achieved.

Figure 2:
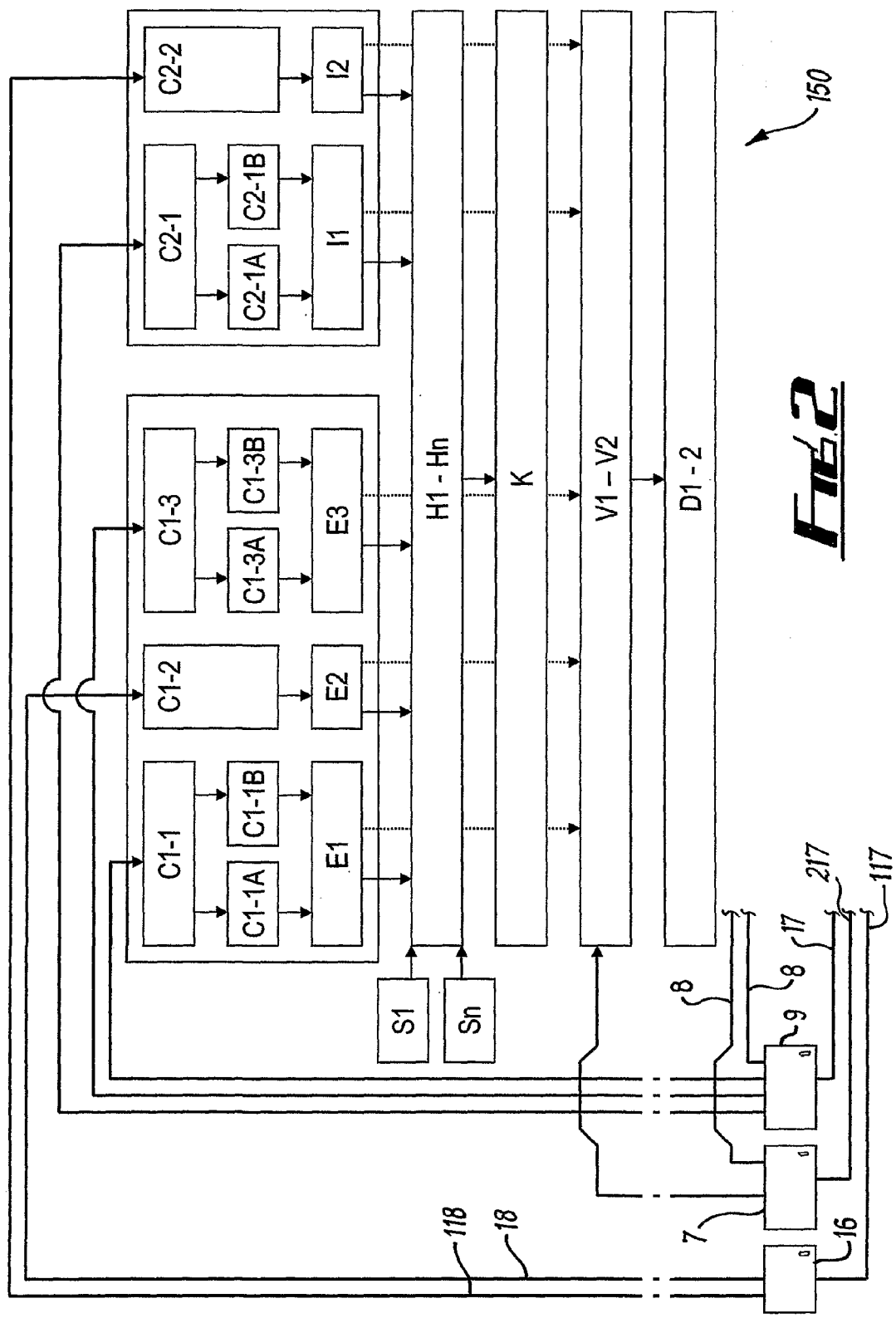
FIG. 2 is a schematic view of a data-processing means in accordance with an alternative embodiment of the invention.

An alternative processing method is shown schematically in FIG. 2 of the drawings, and is carried out using the test apparatus 100 of FIGS. 1, 3 and 4. The system 150 of FIG. 2 is similar to that of FIG. 1, but differs in that provision is made for an additional evaluation of the test objects by means of respective quality criteria which can be preset as analysis thresholds. An appropriate number of analysis thresholds S1 to Sn are preset in this case. At H1 to Hn these can be compared with the signals E1, E2, E3 and I1 to I2 which are fed to this point for evaluation. A appropriate signal indication or output then takes place at step K in the event that, for example, the analysis threshold has been exceeded and the object tested 2 must be rejected. The steps V1-V2 and D1-2 as shown in FIG. 2 are representative of documentation and/or visual indication of the evaluation results.

In the method of FIG. 2, the individual inspection units 3, 4 are calibrated by means of respective calibrating bodies before the three test phases begin. These calibrating bodies are of substantially the same dimensions as the prefabricated parts 2 to be tested, and the properties of their material are substantially the same. The calibration bodies comprise artificially produced instances of damage to the material, the dimensions of which may also be mechanically determined. In a useful embodiment, the calibration defects are made according to the specifications of international standards, such as the specifications of the American Petroleum Institute (API). By using these test defects, which may for example be produced by spark erosion, the sensitivity of the sensor sub-assemblies 3 and 4 is set to suit the amplitude, phase and spacing of the measurement data, in such a way that comparative tests, repeated settings and re-calibration are possible at any time.

Shown in FIGS. 5A to 5C and 6 is an example covering a plurality of API specifications which are relevant to on-site practice. In the table shown in FIG. 6, there are defined by L2, L3 and L4 respective inspection grades which can be applied to the method of testing according to the invention and which are based on artificial reference marks on respective test tubulars 240 (FIG. 5A to 5C). In the example of FIG. 5A, a groove N preset in an interior surface 60 is formed. In FIG. 5B, a groove O is preset in an exterior surface 110, and in FIG. 5C a bore Q is preset in the wall of the tubular. The defects are formed in such a way that these artificial reference marks can be used as a substantially unified API standard for the user of the method of testing of the invention. Shown in the left-hand column of the table in FIG. 6 are the three evaluation grades which are acceptable. and associated with these, in a column T, are the respective depths X of the grooves N, O as a percentage of the given wall thickness of the tube 240. The tolerance on depth in this case is ±15% of the intended depth X of the groove N, O, such that at a minimum groove depth X=0.3 mm, the tolerance on depth may be an amount of approximately ±0.05 mm. Shown in a column R is the length of the groove N, O (at a maximum depth as shown in column T) and in a column W a width S for the groove N, O is assigned to each grade L2, L3, L4. In column Z is an inside diameter K for the bore Q which extends radially to the surface 110.

Taking these geometrical conditions as a basis, the grooves N, O have to be made of a maximum length of 38.1 mm (approximately 1.5 inches) for eddy current measurement and of a length of 50.8 mm (approximately 2 inches) for ultrasonic measurement (at the maximum depth). To calibrate saturation measurements (measurements of stray flux), the length of the groove N, N has to be sized in such a way, according to the particular version of the equipment, so that a repeatable signal can be produced. For this purpose, a tube 240 provided with reference marks is moved, as a part for testing, through the testing unit at the intended speed of inspection. To ensure that the measured values are repeatable, provision is made for the tube for testing 240 to be passed through the testing unit three times.

Having been set to this API standard, the testing sub-assemblies 3, 4 are then used in the on-site testing. The testing sub-assembly 3 is displaced to the further end of the prefabricated part 2, and a reverse displacement of the testing sub-assembly 3 then takes place at constant speed, as indicated by arrow F to make the test. Over this distance of testing P, on-line or real-time evaluation of the measurement data takes place in the data-processing means 200, which is provided in the form of a personal computer.

The above described embodiments are capable of carrying out three test phases, the measurement data from which is combined to provide an assessment of damage condition. However, it is within the scope of the invention to perform and combine the results of two different test phases, selected from conventional eddy current testing; partial saturation eddy current testing and ultrasonics. This combination of two test phases may be any pair wise combination from the above group.

In a preferred embodiment of the invention three test phases are performed using two separate test sub-assemblies. This may be advantageous in circumstances which limit the tool design. For example, for small bore tubulars it may be preferable to avoid running the relatively large-diameter partial saturation eddy current test apparatus from the inside of the tubular. In many applications, it may be preferable to run the external sub-assembly in a first test-pass, and the combination and analysis of the test data from two external test phases may be sufficient to classify the test object (thus negating the requirement of an internal test). Conversely, the combination and analysis of the test data from two internal test phases may be sufficient to classify the test object without an external test.

Figure 7:
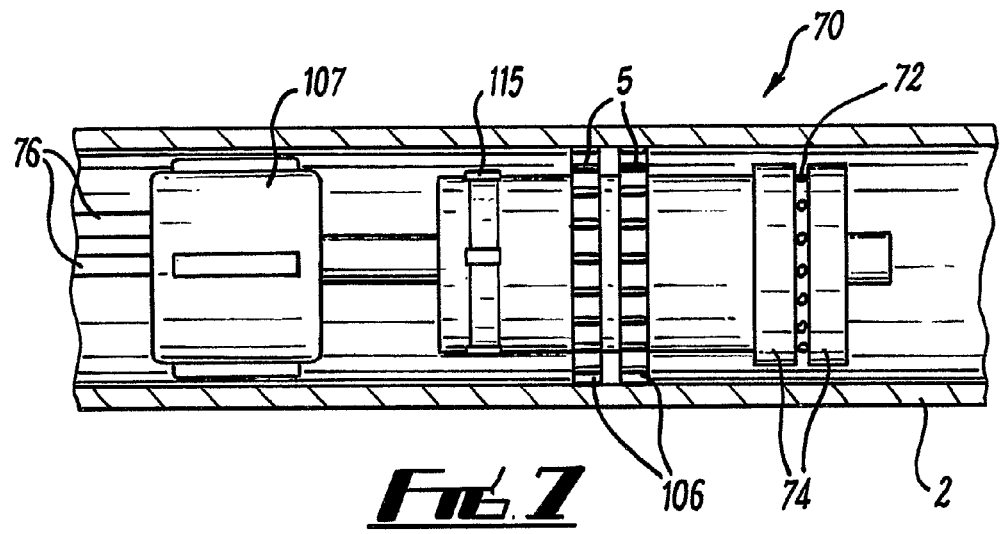
FIG. 7 is a schematic view of an interior sub-assembly in accordance with an alternative embodiment of the invention.

However, according to alternative embodiment of the invention, a single assembly is provided with three test units. FIG. 7 is a schematic view of an internal test assembly, generally depicted at 70, located in a tubular 2. The assembly 70 is similar to sub-assembly 3 (with like parts depicted by the same reference numerals) but differs in that it is provided with partial saturation eddy current sensors 72 located between magnets 74. The ultrasonics sensors 115 are longitudinally spaced from the conventional eddy current testing sensors 5 by approximately 50-100 mm. Similarly, the partial saturation eddy current sensors 72 are longitudinally spaced from the conventional eddy current testing sensors 5 by approximately 50-100 mm. The assembly is capable of carrying out partial saturation eddy current testing, conventional eddy current testing, and ultrasonics testing and outputting the measurement data for analysis via electrical connectors 76. The three test phases may be carried out simultaneously during a single pass of the test object.

Figure 8:
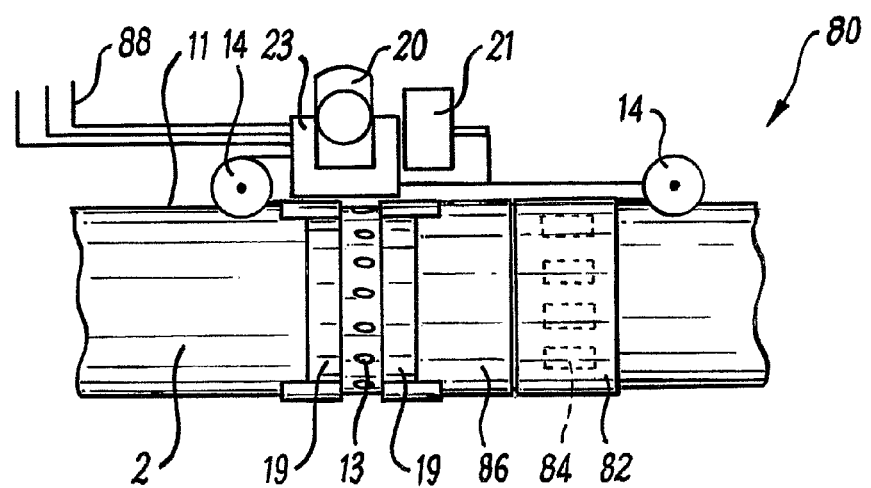
FIG. 8 is a schematic view of an exterior sub-assembly in accordance with an alternative embodiment of the invention.

FIG. 8 is a schematic view of an external test assembly, generally depicted at 80, located on the outer surface 11 of a tubular 2. The assembly 80 is similar to sub-assembly 4 (with like parts depicted by the same reference numerals) but differs in that provided on its body 86 is a housing 82 containing conventional eddy current sensors 84. The assembly is therefore capable of carrying out partial saturation eddy current testing, conventional eddy current testing, and ultrasonics testing and outputting the measurement data for analysis via electrical connectors 88 and as with the assembly of FIG. 7, the three test phases may be carried out simultaneously.

In a further alternative embodiment, the apparatus will be configured such that an assembly or sub-assembly comprises a group of eddy current sensors which may be selectively operated in a partial saturation or a conventional eddy current testing mode.

However, it is preferred to provide a dedicated group of sensors for each mode of eddy current testing, so that each group may be configured for optimal sensitivity in specific frequency bands. In a preferred arrangement, the partial saturation eddy current sensors are multi-differential sensors, configured for detection of circumferential and longitudinal cracking.

In preferred modes of use, the apparatus and method performs a conventional eddy current test at frequencies in the range of 10 kHz to 350 kHz, and most preferably in the range of 100 kHz to 300 kHz.

The partial saturation eddy current testing is preferably performed in a frequency range of 10 kHz to 150 kHz, and most preferably frequencies in the range of 50 kHz to 100 kHz. The present inventors have appreciated that providing a partial saturation of magnetic field and operating within these frequency ranges results in a balance between sensitivity and penetration which is appropriate for the combined analysis techniques of the present invention. For example, the apparatus may be optimally configured for the detection of small volumetric defects, and the partial saturation eddy current test may be configured give strong indications for a subset of the potential defects in the test object.

The invention in one of its aspects relates to a method for the non-destructive testing of casing tubes, riser tubes, pipes, drilling strings or similar prefabricated parts made of electrically conductive metal for exploration, equipping and transporting operations on oil and gas fields, and for producing pipelines and geothermal bores. The prefabricated parts are inspected and assessed as individual test objects prior to installation and are rejected if damage is found which exceeds a limiting value. In accordance with an aspect of the invention at least three test phases are performed on the given test object by means of conventional eddy current testing, partial saturation eddy current testing and ultrasonic testing. In this way, respective test positions giving sets of information on damage may be sensed along pre settable distances of testing (F), the sets of information are brought together in a data-processing means as sets of measurement data from the three tests and all the sets of measurement data are processed by means of a computer program.

In another of its aspects, the invention relates to a method and apparatus in which at least two different test phases are performed on a test object, selected from: conventional eddy current testing, partial saturation eddy current testing, and ultrasonic testing. Measurement data sets are obtained from the at least two different test phases, with each measurement data set comprising measurement data corresponding to a plurality of test positions. The data sets are combined in a data processing means and the combined measurement data is processed to evaluate a damage condition of the test object. In a preferred embodiment, all of conventional eddy current testing, partial saturation eddy current testing, and ultrasonic testing are performed. The apparatus may be provided in two or more sub-assemblies, of which one may be an internal test tool and one may be an external tool. Alternatively, the apparatus may be capable of carrying out all three of the test phases.

Various modifications may be made to the above-described embodiments within the scope of the invention.

The invention claimed is:

1. A method for the non-destructive testing of tubular components made of electrically conductive material, the method comprising the steps of:
   performing at least two different test phases on a test object, the test phases comprising an eddy current test phase and a partial saturation eddy current test phase;
   obtaining a measurement data set from the at least two different test phases, each measurement data set comprising measurement data corresponding to a plurality of test positions; and
   combining the measurement data sets in a data processing means and processing the combined measurement data to evaluate a damage condition of the test object.

2. The method as claimed in claim 1, comprising the step of performing at least three test phases, the test phases selected from the group comprising:
   eddy current testing, partial saturation eddy current testing, and ultrasonic testing.

3. The method as claimed in claim 2, comprising the step of performing eddy current testing, a partial saturation eddy current testing, and ultrasonic testing.

4. The method as claimed in claim 1, comprising an additional step of selecting or rejecting the test object for further use according to the evaluated damage condition.

5. The method as claimed in claim 1, wherein a total number of defects identified in the combined measurement data is used when evaluating the damage condition.

6. The method as claimed in claim 1, wherein a comparison of measurement data from the at least two test phases at a test position is performed by the data-processing means on the test object when evaluating the damage condition.

7. The method as claimed in claim 1, wherein the test object is rejected if a limit value is exceeded in one of the at least two test phases.

8. The method as claimed in claim 1, wherein two test phases are performed simultaneously.

9. The method as claimed in claim 1, wherein two test phases are performed consecutively.

10. The method as claimed in claim 1, wherein the test object is evaluated against quality criteria which are configurable in the data processing means as analysis thresholds.

11. The method as claimed in claim 1, wherein the test object is a tubular member and at least one of the test phases is performed from an interior of the tubular member.

12. The method as claimed in claim 11, wherein the first test phase is performed from an interior of the tubular member and covers an entire cross-section of the tubular member in a single pass of the tubular member.

13. The method as claimed in claim 11, wherein a test phase takes place on an outer circumference of the tubular member, and consists of a single pass of the tubular member.

14. The method as claimed in claim 1, wherein the test object is a tubular member and at least one of the test phases is performed from an exterior of the tubular member.

15. The method as claimed in claim 1, wherein an ultrasonic test is performed from an exterior of the test object.

16. The method as claimed in claim 1, wherein an eddy current testing phase is carried out in a frequency range of 10kHz to 350kHz.

17. The method as claimed in claim 1, wherein a partial saturation eddy current testing phase is carried out in a frequency range of 10kHz to 150kHz.

18. The method as claimed in claim 1, wherein the performance of the partial eddy current test phase comprises step of varying the strength of a magnetic field so as to partially saturate the tubular component.

19. The method as claimed in claim 18, wherein the step of varying the strength of a magnetic field comprises varying a current of an electromagnet.

20. The method as claimed in claim 18, wherein the step of varying the strength of a magnetic field comprises varying distance between a permanent magnet and the tubular component.

21. A method for the non-destructive testing of tubular components made of electrically conductive material, the method comprising the steps of:
performing at least two different test phases on a test object, the test phases comprising an eddy current test phase and a partial saturation eddy current test phase;
obtaining a measurement data set from the at least two different test phases, each measurement data set comprising measurement data corresponding to a plurality of test positions; and
combining the measurement data sets in a data processing means and processing the combined measurement data to evaluate a damage condition of the test object, wherein the test object is a tubular member, and wherein the eddy current test and an ultrasonic test take place from an interior of the tubular member and the partial saturation eddy current test is performed from the outer circumference of the tubular member.

22. Apparatus for the non-destructive testing of tubular components, the apparatus comprising:
sensing apparatus configured to perform at least two different tests on a test object, the tests comprising an eddy current test and a partial saturation eddy current test; and
a data processing means configured to process combined data from at least two measurement data sets from the different tests to evaluate a damage condition of the test object.

23. Apparatus as claimed in claim 22 wherein the sensing apparatus is further configured to perform an ultrasonic test on the test object.

24. Apparatus as claimed in claim 23 comprising a plurality of test components, each component configured to perform one of an eddy current test, a partial saturation eddy current test, and an ultrasonic test.

25. Apparatus as claimed in claim 24 wherein the test components are connected to the data processing means via a multi-channel multiplexer.

26. Apparatus as claimed in claim 24 wherein the test components are operated on a plurality of sub-assemblies.

27. Apparatus as claimed in claim 24 wherein the test components are operated on a single assembly.

28. Apparatus as claimed in claim 22 comprising a sub-assembly configured for interior operation in a test object and a sub-assembly configured for exterior operation on a test object.

29. Apparatus as claimed in claim 22 comprising means for outputting test report parameters.

30. Apparatus as claimed in claim 22 comprising means for registering measurement data according to test position.

31. A method of evaluating a damage condition of a test object, the method comprising the steps of:
combining measurement data sets obtained from a sensing apparatus from at least two different test phases on a test object, the test phases comprising eddy current testing and partial saturation eddy current testing, each measurement data set comprising measurement data corresponding to a plurality of test positions; and
processing the combined measurement data to evaluate a damage condition of the test object.

32. A computer program product embedded in a memory or disk bearing machine readable instructions that, when read and executed by a processor, implement the method of evaluating a damage condition of a test object according to claim 31.

33. A computer apparatus comprising:
a processor; and
one or more computer-readable media having loaded thereon machine readable instructions that, when executed by the processor, implement the method of evaluating a damage condition of a test object according to claim 31.

34. A method for the non-destructive testing of pre-fabricated oilfield tubular components made of electrically conductive material, the method comprising the steps of:
performing at least two different test phases on an oilfield tubular test object, the test phases selected from the group comprising: eddy current testing, partial saturation eddy current testing, and ultrasonic testing;
obtaining a measurement data set from the at least two different test phases, each measurement data set comprising measurement data corresponding to a plurality of test positions;
combining the measurement data sets in a data processing means and processing the combined measurement data to evaluate a damage condition of the oilfield tubular test object.

35. Apparatus for the non-destructive testing of oilfield tubular components, the apparatus comprising:
sensing apparatus configured to perform at least two different tests on an oilfield tubular component test object, the tests selected from: an eddy current test, a partial saturation eddy current test, and an ultrasonic test; and
a data-processing means configured to process combined data from at least two measurement data sets from the different tests to evaluate a damage condition of the test object.

* * * * *